(12) United States Patent
Aronhime et al.

(10) Patent No.: US 6,605,636 B2
(45) Date of Patent: Aug. 12, 2003

(54) ATORVASTATIN HEMI-CALCIUM FORM VII

(75) Inventors: Judith Aronhime, Rehovot (IL); Ramy Lidor-Hadas, Kafar-Saba (IL); Valerie Niddam, Even-Yeouda (IL); Revital Lifshitz, Herzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/992,746

(22) Filed: Nov. 5, 2001

(65) Prior Publication Data

US 2002/0115709 A1 Aug. 22, 2002

Related U.S. Application Data

(60) Provisional application No. 60/245,897, filed on Nov. 3, 2000.

(51) Int. Cl.$^7$ ................... A61K 31/40; C07D 207/335
(52) U.S. Cl. ............................. 514/423; 548/537
(58) Field of Search .................. 548/537; 514/423

(56) References Cited

U.S. PATENT DOCUMENTS

| | | | |
|---|---|---|---|
| 4,681,893 A | 7/1987 | Roth | 514/422 |
| 5,273,995 A | 12/1993 | Roth | 514/422 |
| 5,280,126 A | 1/1994 | Butler et al. | 548/517 |
| 5,969,156 A | * 10/1999 | Briggs et al. | 548/537 |
| 6,087,511 A | 7/2000 | Lin et al. | 548/537 |
| 6,121,461 A | 9/2000 | McKenzie | 548/530 |

FOREIGN PATENT DOCUMENTS

| | | |
|---|---|---|
| WO | WO 97/03958 | 2/1997 |
| WO | WO 97/03959 | 2/1997 |
| WO | WO 01/36384 | 5/2001 |

OTHER PUBLICATIONS

Goodman & Gilman's The Pharmacological Basis of Therapeutics (Ninth Edition), McGraw–Hill, 1996.

The Lancet, article entitled Randomised Trial of cholesterol lowering in 4444 patients with coronary heart disease: the Scandinavian Simvastatin Survival Study (4), The Scandinavian Simvastatin Survival Study Group, vol. 344, Nov. 19, 1994.

Tsutomu Konno, "Physical and Chemical Changes of Medicinals in Mixtures with Adsorbents in the Solid State, IV. Study of Reduced–Pressure Mixing for Practical Use Of Amorphous Mixtures of Flufenamic Acid," 1990 Pharmaceutical Society of Japan, pp. 2003–2007.

Roth et al., "Inhibitors of Cholesterol Biosynthesis. 3. Tetrahdro–4–hydroxy–6–[2–(1H–pyrrol–1–yl)ethyl]–2H–pyran–2–one Inhibitors of HMG–CoA Reductase.2. Effects of Introducing Substituents at Positions Three and Four of the Pyrrole Nucleus," 1991 American Chemical Society, pp. 357–366.

Baumann et al., "The Convergent Synthesis of CI–981, an Optically Active, Highly Potent, Tissue Selective of HMG–CoA Reductase," Tetrahedron Letters, vol. 33, No. 17, 1992, pp. 2283–2284.

Brower et al., "The Synthesis of (4R–cis)–1,1–Dimethylethyl 6–cyanomethyl–2,2–dimethyl–1, 3–dioxane–4–acetate, a Key Intermediate for the Preparation of CI–981, a Highly Potent, Tissue Selective Inhibitor of MG–CoA Reductase," Tetrahedron Letters, vol. 33, No. 17, 1992, pp. 2279–2282.

Kearney et al., "The Interconversion Kinetics, Equilibrium, and Solubilities of the Lactone and Hydroxyacid Forms of the MMG–CoA Reductase Inhibitor, CI–981," Pharmaceutical Research, vol. 10, No. 10, 1993, pp. 1461–1465.

* cited by examiner

Primary Examiner—Fiona T. Powers
(74) Attorney, Agent, or Firm—Kenyon & Kenyon

(57) ABSTRACT

The present invention provides a novel form of atorvastatin hemi-calcium designated Form VII and novel processes for its preparation whereby another crystalline form of atorvastatin hemi-calcium is suspended in ethanol, preferably absolute ethanol, and is converted to the new form, which is then isolated. The present invention further provides a method of reducing the plasma low density lipoprotein level in patients suffering from or susceptible to hypercholesterolemia and compositions and dosage forms for practicing the invention.

17 Claims, 1 Drawing Sheet

ATORVASTATIN HEMI-CALCIUM FORM VII

CROSS-REFERENCE TO RELATED APPLICATIONS

This application claims the benefit of provisional application Serial No. 60/245,897, filed Nov. 3, 2000 which is incorporated herein by reference.

FIELD OF THE INVENTION

The present invention relates to crystalline polymorphic forms of atorvastatin hemi-calcium and novel processes for preparing crystalline solids.

BACKGROUND OF THE INVENTION

Atorvastatin, ([R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid), depicted in lactone form in formula (I) and its calcium salt of formula (II) are known in the art, and described, in U.S. Pat. No. 4,681,893, 5,273,995, and in commonly-assigned, co-pending U.S. Ser. No. 60/166,153, filed Nov. 17, 2000, all of which are herein incorporated by reference.

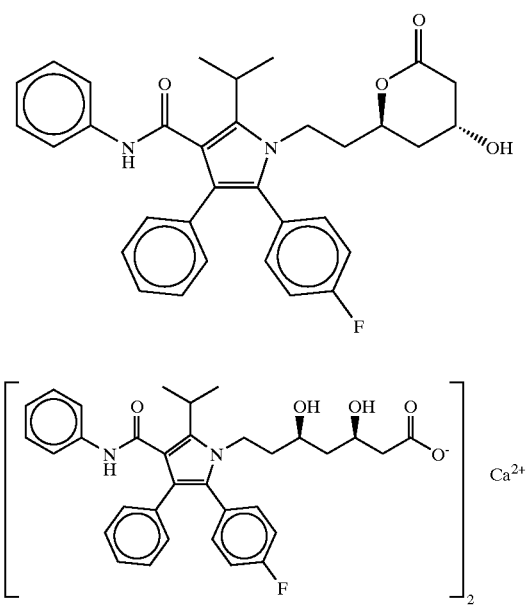

Atorvastatin is a member of the class of drugs called statins. Statin drugs are currently the most therapeutically effective drugs available for reducing low density lipoprotein (LDL) particle concentration in the blood stream of patients at risk for cardiovascular disease. A high level of LDL in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and patients who are free of cardiovascular disease but who have hypercholesterolemia. Scandinavian Simvastatin Survival Study Group, 1994; Lipid Research Clinics Program, 1984a, 1984b.

The mechanism of action of statin drugs has been elucidated in some detail. They interfere with the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion HMG to mevalonate, which is the rate determining step in the biosynthesis of cholesterol, and so, its inhibition leads to a reduction in the concentration of cholesterol in the liver. Very low density lipoprotein (VLDL) is the biological vehicle for transporting cholesterol and triglycerides from the liver to peripheral cells. VLDL is catabolized in the peripheral cells which releases fatty acids which may be stored in adopcytes or oxidized by muscle. The VLDL is converted to intermediate density lipoprotein (IDL), which is either removed by an LDL receptor, or is converted to LDL. Decreased production of cholesterol leads to an increase in the number of LDL receptors and corresponding reduction in the production of LDL particles by metabolism of IDL.

Atorvastatin hemi-calcium salt trihydrate is marketed under the name LIPITOR by Warner-Lambert Co. Atorvastatin was first disclosed to the public and claimed in U.S. Pat. No. 4,681,893. The hemi-calcium salt depicted in formula (II) is disclosed in U.S. Pat. No. 5,273,995. The '995 patent teaches that the hemi-calcium salt is obtained by crystallization from a brine solution resulting from the transposition of the sodium salt with $CaCl_2$ and further purified by recrystallization from a 5:3 mixture of ethyl acetate and hexane.

The present invention provides a new crystal form of atorvastatin hemi-calcium. The occurrence of different crystal forms (polymorphism) is a property of some molecules and molecular complexes. A single molecule, like the atorvastatin in formula (I) or the salt complex of formula (II), may give rise to a variety of solids having distinct physical properties like melting point, X-ray diffraction pattern, infrared absorption fingerprint and NMR spectrum. The differences in the physical properties of polymorphs result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. On the other hand, where the effectiveness of a drug correlates with peak bloodstream levels of the drug, a property shared by statin drugs, and provided the drug is rapidly absorbed by the GI system, then a more rapidly dissolving form is likely to exhibit increased effectiveness over a comparable amount of a more slowly dissolving form.

Crystalline Forms I, II, III and IV of atorvastatin hemi-calcium are the subjects of U.S. Pat. Nos. 5,969,156 and 6,121,461 assigned to Warner-Lambert and crystalline atorvastatin hemi-calcium Form V is disclosed in commonly-owned, co-pending application Ser. No. 09/714,351. There is an assertion in the '156 patent that Form I possesses more favorable filtration and drying characteristics than the known amorphous form of atorvastatin hemi-calcium. Although Form I remedies some of the deficiencies of the amorphous material in terms of manufacturability, there remains a need for yet further improvement in these properties as well as improvements in other properties such as flowability, vapor impermeability and solubility. The discovery of a new crystalline polymorphic form of a drug enlarges the repertoire of materials that a formulation scientist has with which to design a pharmaceutical dosage form of a drug with a targeted release profile or other desired characteristic.

SUMMARY OF THE INVENTION

Figure 1:
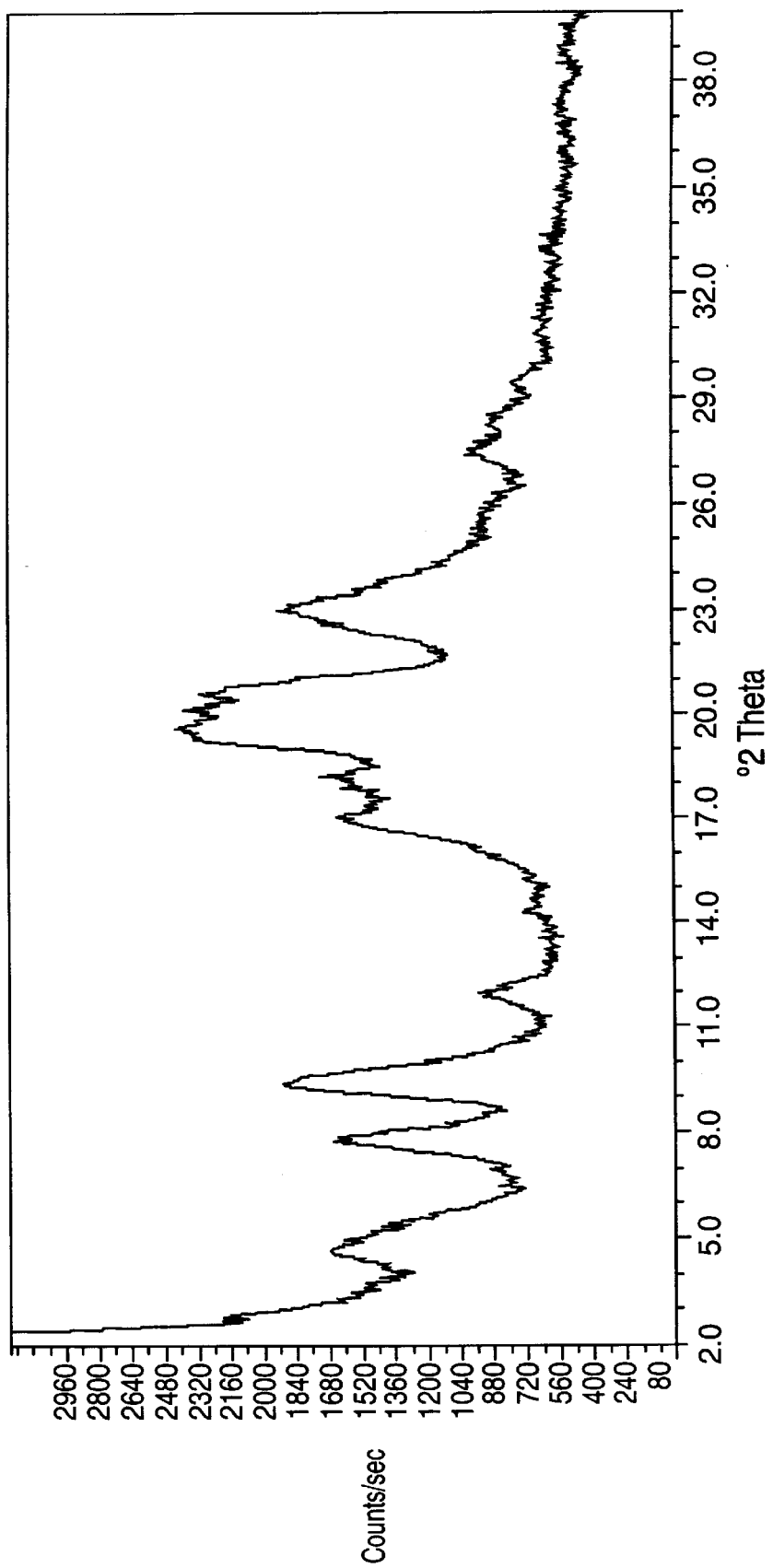
FIG. 1 is a characteristic powder X-ray diffraction pattern of atorvastatin hemi-calcium Form VII.

The present invention provides a novel crystalline form of atorvastatin hemi-calcium denominated Form VII, hydrates thereof and novel processes for its preparation.

In another aspect, the invention provides compositions and dosage forms comprising atorvastatin hemi-calcium Form VII.

In yet another aspect, the invention provides a method of reducing plasma low density lipoprotein level in a patient suffering from or susceptible to hypercholesterolemia by administering to the patient a pharmaceutical dosage form containing atorvastatin hemi-calcium Form VII.

DETAILED DESCRIPTION OF THE PREFERRED EMBODIMENTS

The present invention provides a new crystalline polymorphic form of atorvastatin that has been designated Form VII in keeping with the established nomenclature for this organic salt. Atorvastatin hemi-calcium Form VII is characterized by and distinguishable from other forms by a powder X-ray diffraction pattern (FIG. 1) having two broad peaks in the range 18.5–21.8 and 21.8–25.0 degrees 2θ and other broad peaks at 4.7, 7.8, 9.3, 12.0, 17.1, 18.2±0.2 degrees 2θ. Samples of Form VII may contain up to 12% water. Form VII is readily distinguished from known forms of atorvastatin hemi-calcium by the broad peaks at 7.8 and 9.3±0.2 degrees 2θ. For instance, Form I has peaks at 9.2, 9.5, 10.3, 10.6, 11.0 and 12.2 degrees 2θ according to the information provided in U.S. Pat. No. 5,969,156. In this region, Form II has two sharp peaks at 8.5 and 9.0 degrees 2θ and Form IV has one strong peak at 8.0 degrees 2θ. The other broad peaks in the region of 15–25 degrees 2θ distinguish Form VII from all other forms. Forms I, III and IV all have sharp peaks in this region. Powder X-ray diffraction ("PXRD") data was obtained by methods known in the art using a SCINTAG powder X-ray diffractometer model X'TRA equipped with a solid-state detector. Copper radiation of $\lambda=1.5418$ Å was used.

Atorvastatin hemi-calcium Form VII may be prepared by treating atorvastatin hemi-calcium Forms I or V with ethanol, preferably absolute ethanol, at room temperature to reflux temperature for a period of from about 1 h to about 24 h, preferably 2.5–16 h. The rate of the conversion of Form I or V to Form VII is temperature dependent. A preferred operating temperature range is from about 20° C. to about 78° C. Complete conversion has been observed in as little as about 2.5 h in a suspension in refluxing EtOH. If the process is carried out at room temperature a longer period is required. After the conversion is complete, the crystals of Form VII may be isolated conventionally, such as by filtration, and dried. A temperature of about 65° C., ambient pressure and 24 hours drying time are suitable conditions for drying the crystals.

The starting material atorvastatin hemi-calcium Form I may be prepared by following the procedures of Example 1 of U.S. Pat. No. 5,969,156, which patent is hereby incorporated by reference in its entirety. According to one method, a mixture of atorvastatin lactone prepared according to a procedure described in U.S. Pat. No. 5,273,995, which also is hereby incorporated by reference in its entirety, methyl tertiary-butyl ether (MTBE) and methanol is reacted with an aqueous solution of sodium hydroxide at 48–58° C. for 40 to 60 minutes to form the sodium salt of atorvastatin free acid. After cooling to 25–35° C., the organic layer is discarded, and the aqueous layer is again extracted with MTBE. The organic layer is discarded, and the MTBE saturated aqueous solution of the sodium salt is heated to 47–52° C. To this solution is added a solution of calcium acetate hemihydrate dissolved in water over at least 30 minutes. The mixture is seeded with a slurry of crystalline Form I atorvastatin shortly after addition of the calcium acetate solution. The mixture is then heated to 51–57° C. for at least 10 minutes and then cooled to 15–40° C. The mixture is filtered, washed with a solution of water and methanol followed by water. The solid is dried at 60–70° C. under vacuum for 3 to 4 days to give crystalline Form I atorvastatin.

Another suitable starting material, atorvastatin hemi-calcium Form V, may be prepared by crystallization from mixtures of tetrahydrofuran, methanol or ethanol with water. For example, atorvastatin hemi-calcium may be dissolved in methanol (e.g. at 0.025–0.050 g/ml). The solution may be warmed to about 60° C. and then an approximately equal volume or less of water is added. The solution is then cooled, which, in combination with the added water, induces atorvastatin hemi-calcium to crystallize in polymorphic Form V. Ethanol and THF may be readily substituted for methanol in this procedure, although when THF is used, it is preferable to add an excess volume of water.

Atorvastatin hemi-calcium Form VII is useful for reducing the plasma low density lipoprotein level of a patient suffering from or susceptible to hypercholesterolemia. For this purpose, it will typically be administered to human patients in a unit dose of from about 0.5 mg to about 100 mg. For most patients, a dose of from about 2.5 to about 80 mg per day, more particularly from about 2.5 to about 20 mg per day, causes a lowering of the plasma low density lipoprotein. Whether such lowering is sufficient or whether the dose or dose frequency should be increased is a determination that is within the skill level of appropriately trained medical personnel.

A further aspect of the present invention is a pharmaceutical composition and dosage form containing the novel form of atorvastatin hemi-calcium that may be administered in the practice of the method of the invention.

The compositions of the invention include powders, granulates, aggregates and other solid compositions comprising novel Form VII of atorvastatin hemi-calcium. In addition, Form VII compositions that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in a solid composition of Form VII atorvastatin hemi-calcium further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The Dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of atorvastatin hemi-calcium whereupon the properties that distinguish the solid forms of atorvastatin hemi-calcium are lost. However, the use of the novel forms to prepare such solutions (e.g. so as to deliver, in addition to atorvastatin, a solvate to said solution in a certain ratio with a solvate) is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Having thus described the invention with reference to particular preferred embodiments, the following examples are provided to further illustrate the invention. They are not intended to be limiting in any way.

EXAMPLES

General

Absolute ethanol containing less than 0.2% water was purchased from Biolab®. Other reagents were reagent grade and were used as received.

Example 1

Atorvastatin hemi-calcium Form V (1.00 g) was stirred in absolute EtOH (400 ml) at room temperature for 16 h. The solid was collected by filtration and dried at 65° C. for 24 h to give atorvastatin hemi-calcium Form VII (40 mg, 40%).

Example 2

Atorvastatin hemi-calcium Form I (75 mg) was stirred in absolute EtOH (30 ml) at room temperature for 16 h. The solid was collected by filtration and dried at 65° C. for 24 h to give atorvastatin hemi-calcium Form VII (0.60 g, 80%).

Having thus described the invention with reference to particular preferred embodiments and illustrated it with examples, those in the art may appreciate modifications to the invention as described and illustrated that do not depart from the spirit and scope of the invention as defined by the claims which follow.

We claim:

1. Atorvastatin hemi-calcium Form VII or a hydrate thereof having a powder X-ray diffraction pattern substantially as depicted in FIG. 1.

2. Atorvastatin hemi-calcium Form VII or a hydrate thereof characterized by a powder X-ray diffraction pattern having broad peaks in the range of 18.5–21.8 and 21.8–25.0 degrees two-theta.

3. The atorvastatin hemi-calcium Form VII or a hydrate thereof of claim 2 further characterized by broad peaks at 4.7, 7.8, 9.3, 12.0, 17.1, 18.2±0.2 degrees 2θ in its powder X-ray diffraction pattern.

4. The atorvastatin hemi-calcium Form VII or a hydrate thereof of claim 2 containing up to about 12% water.

5. The atorvastatin hemi-calcium Form VII or a hydrate thereof of claim 2 containing from about one to about eight moles of water per mole of atorvastatin hemi-calcium.

6. The atorvastatin hemi-calcium Form VII or a hydrate thereof of claim 2 having a narrow particle size distribution.

7. The atorvastatin hemi-calcium Form VII or a hydrate thereof of claim 6 wherein all of the particles are 100 microns or less in diameter.

8. The atorvastatin hemi-calcium Form VII or a hydrate thereof of claim 7 wherein all of the particles are 50 microns or less in diameter.

9. A process for preparing atorvastatin hemi-calcium Form VII comprising the steps of:

a) suspending atorvastatin hemi-calcium in ethanol for a period of time sufficient to convert it into Form VII and b) recovering Form VII from the suspension.

10. The process for preparing atorvastatin hemi-calcium Form VII of claim 9 wherein the suspension is maintained at a temperature in the range of from about 20° C. to about 78° C. for the period of time in which the atorvastatin hemi-calcium is converted into Form VII.

11. The process of claim 9 wherein the atorvastatin hemi-calcium is Form I or Form V.

12. The process of claim 9 wherein the ethanol contains less than about 0.5% water.

13. The process of claim 12 wherein the ethanol contains less than about 0.2% water.

14. A pharmaceutical composition comprising the atorvastatin hemi-calcium Form VII or a hydrate thereof of claim 2.

15. A pharmaceutical dosage form comprising the pharmaceutical composition of claim 14.

16. A method of reducing the plasma low density lipoprotein level of a patient suffering from or susceptible to hypercholesterolemia by administering to the patient a pharmaceutical dosage form of claim 15.

17. A process for preparing a pharmaceutical dosage form comprising admixing the atorvastatin hemi-calcium Form VII or hydrate thereof of claim 2 and a pharmaceutically acceptable carrier.

* * * * *